United States Patent [19]

Ohlendorf et al.

[11] Patent Number: 5,710,307
[45] Date of Patent: Jan. 20, 1998

[54] PROCESS FOR THE PRODUCTION OF TRIALKYL PHOSPHITES

[75] Inventors: Wolfgang Ohlendorf; Hans-Dieter Block, both of Leverkusen, Germany

[73] Assignee: Bayer AG, Leverkusen, Germany

[21] Appl. No.: 802,712

[22] Filed: Feb. 19, 1997

[30] Foreign Application Priority Data

Feb. 28, 1996 [DE] Germany ................ 19607459.2

[51] Int. Cl.$^6$ ................................................. C07F 9/142
[52] U.S. Cl. ................................................. 558/96
[58] Field of Search ................................................. 558/96

[56] References Cited

U.S. PATENT DOCUMENTS 2,408,744 10/1946 Engel ........................... 558/96
2,848,474 8/1958 Marshall ........................ 558/96

FOREIGN PATENT DOCUMENTS 2821 7/1979 European Pat. Off. .
D. 1 024 944 2/1958 Germany .

OTHER PUBLICATIONS

Orbit Abstract of EP 0 002 821 (Jul. 11, 1979).

WPI Abstract Accession No. 96–441047/44 & KR 950000194 B1 (Kumho Shell Chem) Nov. 1, 1995.

*Methoden der organischen Chemie* (Houben–Weyl), vol. XII/2, pp. 53–78, G. Thieme Verlag, Stuttgart (1964).

Supplement E1 *Methoden der organischen Chemie* (Houben–Weyl), vol. XII/2, pp. 413–421, G. Thieme Verlag, Stuttgart (1964).

*Primary Examiner*—Michael G. Ambrose
*Attorney, Agent, or Firm*—Connolly & Hutz

[57] ABSTRACT

This invention relates to a process for the production of symmetrical trialkyl phosphites, which are also known as phosphorus acid trialkyl esters, from phosphorus trichloride and alcohol in the presence of an auxiliary base as an acid-binding agent and a solvent.

16 Claims, No Drawings

PROCESS FOR THE PRODUCTION OF TRIALKYL PHOSPHITES

This invention relates to a process for the production of symmetrical trialkyl phosphites, which are also known as phosphorous acid trialkyl esters, from phosphorus trichloride and alcohol in the presence of an auxiliary base as an acid-binding agent and a solvent.

Trialkyl phosphites are highly economically significant intermediate products produced on a large industrial scale. A whole range of processes for the synthesis of trialkyl phosphites has thus been developed. The manual *Methoden der organischen Chemie* (Houben-Weyl), volume XII/2, pages 53–78, G. Thieme Verlag, Stuttgart 1964 and the associated supplement E1, pages 413–421, Stuttgart, New York 1982 give a comprehensive review of possible synthesis methods. Of the possible synthesis methods stated therein, only direct synthesis from phosphorus trichloride and alcohol in the presence of an auxiliary base and transesterfication of phosphorous acid trialkyl esters (trialkyl phosphites) and phosphorous acid ester amides with alcohols have proved economically viable. The latter-stated phosphorous acid trialkyl esters and phosphorous acid alkyl ester amides are in turn obtained from phosphorus trichloride and alcohols and secondary and/or tertiary amines. Trialkyl phosphite synthesis thus always starts from phosphorus trichloride and alcohol in the presence of an auxiliary base, generally an amine or ammonia.

Hitherto known processes used industrially for the production of symmetrical trialkyl phosphites from phosphorus trichloride and alcohol in the presence of an auxiliary base and an inert solvent, such as for example ethers, chlorinated hydrocarbons, petroleum ether, naphtha, petroleum fractions, benzene or butane, however, suffer the disadvantage that the hydrochlorides of the auxiliary bases used are insoluble in the system comprising the resultant trialkyl phosphite and solvent and as yet unreacted stag materials. This situation is particularly disadvantageous industrially as not only is the miscibility and stirrability of the entire system dramatically reduced, so that the exchange of heat and materials is considerably impeded, but also because the insoluble solid is preferentially deposited on heat exchange surfaces and stirring devices and in areas of low flow and, finally, because it dramatically restricts the options for distilling the trialkyl phosphite directly from the reaction mixture without a reduction in yield, as proposed in German patent 1 024 944. The process proposed in German patent 1 024 944 thus remits in only comparatively poor yields and has thus not found any practical application.

The only processes to be used industrially are those in which the precipitated amine hydrochloride or ammonium chloride is initially separated from the reaction mixture produced from phosphorus trichloride, alcohol and auxiliary base in an inert solvent, for example by washing with water or with aqueous solutions or by filtration. Removing the amine hydrochloride or ammonium chloride by washing has inter alia the major disadvantage that the introduced water always results in partial hydrolysis of the trialkyl phosphite to yield dialkyl phosphite, wherein this conversion is catalysed by traces of acid, so reducing the yield of the desired trialkyl phosphite. While filtering out the amine hydrochloride or ammonium chloride does indeed avoid this reduction in yield caused by hydrolysis, this process is technically very complex. Furthermore, despite considerable efforts, even with repeated extraction of the filter cake with large quantities of fresh solvent, which have to be recycled, it is not possible to remove all the adhering and enclosed trialkyl phosphite from the filter cake, so resulting in this case too, despite considerable operational complication, in a reduction in yield.

These complicated, yield-reducing separation measures for the undissolved hydrochloride are taken only because the problems caused by the undissolved hydrochloride during isolation of the desired trialkyl phosphite are incomparably greater.

The object of the present invention was to provide a process which allows the production of trialkyl phosphites from phosphorus trichloride and alcohol in the presence of an auxiliary base in a homogeneous liquid phase without producing solid reaction products.

The present invention provides a process for the production of trialkyl phosphites by reacting phosphorus trichloride with the corresponding alcohols in an inert solvent in the presence of an auxiliary base, which process is characterised in that alkyl aromatics having more than 50 wt. % of aromatic carbon atoms, molecular weights of 106 to 150, preferably of 120 to 140, and boiling points of below 220° C. at standard pressure are used as the solvent and alkylamines having more than 10 carbon atoms are used as the auxiliary base.

Considerably higher yields may be achieved using the process according to the invention than using hitherto known processes.

Particularly suitable inert solvents which may be cited by way of example are trimethylbenzenes, isopropylbenzene, butylbenzene, diethylbenzene, 1,2,3,4- and 1,2,3,5-tetramethylbenzene. Tetralin (tetrahydronaphthalene) is a particularly preferred solvent.

Particularly suitable alkylamines having more than 10 carbon atoms which may be cited are tributylamine, tripentylamine, trihexylamine, dibutyloctylamine, trioctylamine, tridecylamine and dioctylamine. Mixtures of such amines may also be used.

Tributylamine is particularly preferred as the alkylamine.

It is known to react phosphorus bichloride with alcohols in the presence of amines at temperatures of approximately −20° C. to approximately 100° C., preferably of 0° C. to 40° C. and with thorough stirring. Since the reaction proceeds very rapidly within the stated temperature range, special measures to complete the reaction, such as for example long periods of stirring, are not generally necessary.

The molar ratio of the components to be used phosphorus trichloride:alcohol:amine is between 1:3.0:3.0 and 1:3.3:3.3, wherein, while smaller proportions of alcohol and amine are indeed in principle possible, they are inappropriate for economic performance of the reaction because secondary reactions then necessarily proceed to a greater extent. The above-stated reaction conditions are also suitable for the process according to the invention.

The quantity of solvent is preferably selected in such a manner that the concentration of trialkyl phosphite in the reaction mixture is between 2 wt. % and 10 wt. % and the associated concentration of amine hydrochloride is no less than 8 wt. %.

The quantity of solvent is particularly preferably adjusted to a concentration of 4 to 7 wt. % of trialkyl phosphite in the completely reacted reaction mixture.

The process according to the invention may be performed both batch-wise and as a continuous process. In the batch-wise reaction, both the solvent and a mixture of solvent and amine and a mixture of solvent and alcohol and a mixture of solvent, amine and alcohol may initially be introduced and the remaining components subsequently added in the correct ratio. In principle, all the reactants may be mixed in any desired sequence, provided that it is ensured that the quantity of amine present in the reaction mixture is at all times at least approximately three times the molar quantity of phosphorus trichloride present and provided that the quantity of solvent contained in the reaction mixture is at all times sufficiently large to dissolve the amine hydrochloride produced.

The process according to the invention is particularly advantageously performed in combination with distillative separation of the resultant trialkyl phosphite, in particular if the resultant trialkyl phosphite has a lower boiling point than the solvent used. The trialkyl phosphite is preferably separated from the reaction mixture under reduced pressure using known separation apparatus, such as distillation columns. A pressure allowing the inert solvent to boil at below 100° C. and a short residence time column, i.e. a column with a small operating hold-up, are particularly preferred. The solution to be separated is preferably introduced more than one theoretical plate above the boiling column bottom of the column. The process according to the invention in combination with distillative separation of the resultant trialkyl phosphite under reduced pressure is particularly advantageously applicable in the production of dimethyl phosphite and triethyl phosphite.

Other methods for working up such reaction mixtures, which substantially contain trialkyl phosphite, amine hydrochloride and solvent, are of course also possible, for example removing the amine hydrochloride by washing with water or aqueous solutions and subsequent distillative separation of the remaining fraction undissolved in water substantially consisting of trialkyl phosphite and solvent. Secondary constituents, in particular excess amine and/or alcohol, which are present in addition to the stated main components are either removed by distillation as low-boiling components before the other components or, in the case of a washing process, pass partially or entirely into the water phase.

The solution substantially consisting of solvent and amine hydrochloride remaining after distillative separation of the resultant trialkyl phosphite may be converted into a reusable solution of amine and solvent by adding bases, for example alkali metal or alkaline earth metal hydroxides, oxides or carbonates, wherein drying, for example by partial distillation, is sensibly performed prior to reuse. Of course, the amine hydrochloride may also first be extracted from the solvent with water. A base is added to the resultant aqueous solution of the amine hydrochloride, as it may be to any aqueous solution obtained on extraction of the amine hydrochloride from the reaction mixture (solvent, trialkyl phosphite and amine hydrochloride), in order to convert the amine hydrochloride into the free amine. In this manner, it is possible not only separately to recover and treat the solvent and free amine but also to extract the released amine from the aqueous solution with the solvent.

Components introduced in excess and not consumed for synthesis of the trialkyl phosphite, such as amine and alcohol, are preferably recovered and reused.

Using the process according to the invention, it is possible to produce trialkyl phosphites without solids and thus in a single phase. In all hitherto known processes, the trialkyl phosphite was produced in a two-phase system, with all the associated disadvantages. A single phase system was not obtained until the reaction mixture was worked up by additional measures, such as filtration or washing.

The process according to the invention allows trialkyl phosphites to be obtained in a technically simple manner and without any risk of a reduction in yield by hydrolysis.

The following examples are intended to illustrate the invention.

EXAMPLES

Example 1

920 g of Tetralin, 305 g of tri-n-butylamine and 53 g of methanol were initially introduced into a reaction apparatus which had been purged with inert gas. 69 g of phosphorus trichloride were added with cooling and vigorous stirring to this mixture within approximately 20 minutes, such that the temperature of the mixture did not exceed 40° C.

On completion of addition, a clear solution containing no solids was obtained. Approximately 97% of the phosphorus trichloride were converted into trimethyl phosphite. A proportion of approximately 3% of the secondary product dimethyl phosphite was produced.

Example 2

713 g of Tetralin, 305 g of tri-n-butylamine and 53 g of methanol were initially introduced into a reaction apparatus which had been purged with inert gas. 69 g of phosphorus trichloride in 241 g of Tetralin were added with cooling and vigorous stirring to this mixture, such that the temperature of the mixture did not exceed 40° C.

As in Example 1, a clear solution containing no solids was obtained on completion of addition. As in Example 1, conversion to the product proceeded to a yield of approximately 97%.

Example 3

8590 g/h of Tetralin (65 mol/h), 686 g/h of ethanol (14.9 mol/h), 2750 g/h of tri-n-butylamine (14.9 mol/h) and 621 g/h of phosphorus trichloride (4.5 mol/h) were pumped into a reaction vessel.

The reaction mixture was maintained at approximately 35° C. by cooling with water. The completely reacted, homogeneous mixture continuously flowed over an overflow into a cooled holding vessel maintained at 35° C. A metering pump was used to draw off from this holding vessel a quantity of reaction mixture (on average approximately 12.6 kg/h) sufficient to ensure that the liquid level remained constant. The metering pump conveyed the liquid into a column 1 packed with wire helices having approximately 20 theoretical plates. The liquid was introduced half way up column 1. The head pressure of the column was 50 mbar. Once steady-state operation was achieved, approximately 800 g/h of condensate (average composition: 735 g/h of triethyl phosphite and 55 g/h of ethanol) were drawn off at the head of the column at a head temperature of 40.5° C. and passed into a receiver evacuated to 50 mbar, from which the mixture was passed by means of a metering pump into a packed column 2 operated at standard pressure having approximately 10 theoretical plates, in which the lower-boiling ethanol was driven off. The yield was 734 g/h of triethyl phosphite. Approximately 8590 g/h of Tetralin, approximately 240 g/h of tributylamine and approximately 3000 g/h tributylammonium chloride (tributylamine hydrochloride) were drawn off as the bottom product at a temperature of 113° C. from the heated column bottom of the column 1 operated under a vacuum. Heating was arranged such that a temperature of 106° to 107° C. was maintained at the lower end of the upper quarter of the column at a reflux ratio R/E adjusted to a constant 15 at the head of the column.

The column bottoms were reconverted into a mixture of tributylamine and Tetralin with sodium hydroxide solution, which, once the mixture had been distilled, wherein the water was also separated, was returned to the process.

What is claimed is:

1. A process for the production of trialkyl phosphites comprising the following steps:

forming a reaction mixture consisting essentially of phosphorus trichloride, an alcohol, a solvent and an auxiliary base, characterised in that at least one alkyl amine having more than 10 carbon atoms is used as the auxiliary base, at least one alkyl aromatic having more than 50 wt. % of aromatic carbon atoms, a molecular weight of from 106 to 150 and a boiling point of below 220° C. at standard pressure is used as the solvent and the alcohol has an alkyl group and a hydroxy group and the alkyl group of the alcohol is the same as the alkyl group of the trialkyl phosphite, and reacting the phosphorus trichloride with the alcohol in the solvent in the presence of the auxiliary base to form a reaction product.

2. The process according to claim 1, characterised in that Tetralin is used as the solvent.

3. The process according to claim 1, characterised in that tributylamine is used as the auxiliary base.

4. The process according to claim 1, characterized in that the molar ratio of phosphorus trichloride:alcohol:amine in the reaction mixture is between 1:3.0:3.0 and 1:3.3:3.3 and the amount of solvent in the reaction mixture is sufficient so that the concentration of trialkyl phosphite in the reaction mixture is between 2 and 10 wt. %.

5. The process according to claim 1, characterised in that, after the reaction, the reaction product is separated in a distillation column having a small operating hold-up into a head product containing said trialkyl phosphite and a bottom product containing said solvent and an alkylamine hydrochloride.

6. A process for the production of a trialkyl phosphite comprising the following steps:

a) forming a reaction mixture consisting essentially of phosphorus trichloride, an alcohol, a solvent and an auxiliary base, wherein said auxiliary-base is an alkylamine having more than 10 carbon atoms, said alcohol has an alkyl group and a hydroxy group and the alkyl group of the alcohol is the same as the alkyl group of the trialkyl phosphite, and said solvent is an alkyl aromatic having more than 50 wt. % of aromatic carbon atoms, a molecular weight of from 106 to 150 and a boiling point of below 220° C. at standard pressure;

b) reacting the phosphorus trichloride with the alcohol in the solvent in the presence of the auxiliary base to form a reaction product; and c) separating the trialkyl phosphite from the reaction product.

7. The process according to claim 6, wherein the auxiliary base is a trialkylamine.

8. The process according to claim 6, wherein the solvent is selected from the group consisting of trimethylbenzenes, isopropylbenzene, butylbenzene, diethylbenzene, 1, 2, 3, 4- and 1, 2, 3, 5-tetramethylbenzene.

9. The process according to claim 6, wherein the solvent is Tetralin.

10. The process according to claim 6, wherein the auxiliary base is selected from the group consisting of tributylamine, tripentylamine, trihexylamine, dibutyloctylamine, trioctylamine, tridecylamine and dioctylamine.

11. The process according to claim 6, wherein the auxiliary base is tributylamine.

12. The process according to claim 6, wherein the solvent has a molecular weight of from about 120 to 140.

13. The process according to claim 6, wherein the trialkyl phosphite is separated from the reaction product by distillation.

14. The process according to claim 6, wherein the reaction product consists essentially of said trialkylphosphite, said solvent, said alcohol, said auxiliary base and a hydrochloride of said auxiliary base and further wherein the reaction product is separated in a distillation column having a small operating hold-up into a head product consisting essentially of said trialkyl phosphite and said alcohol and a bottom product consisting essentially of said solvent, said auxiliary base and said hydrochloride of said auxiliary base.

15. The process according to claim 14, wherein said auxiliary base is a trialkylamine having more than 10 carbon atoms and said hydrochloride of said auxiliary base is trialkylamine hydrochloride.

16. The process according to claim 14, wherein said auxiliary base is tributylamine and said hydrochloride of said auxiliary base is tributylamine hydrochloride.

* * * * *

UNITED STATES PATENT AND TRADEMARK OFFICE
CERTIFICATE OF CORRECTION

PATENT NO. : 5,710,307
DATED : January 20, 1998
INVENTOR(S) : Wolfgang Ohlendorf, et al.

It is certified that error appears in the above-indentified patent and that said Letters Patent is hereby corrected as shown below:

In Column 5, line 43 (Claim 6), "auxiliary-base" should read --auxiliary base--.

Signed and Sealed this

Fourteenth Day of July, 1998

Attest:

BRUCE LEHMAN

Attesting Officer

Commissioner of Patents and Trademarks